US008460693B2

(12) United States Patent
Dhondt et al.

(10) Patent No.: US 8,460,693 B2
(45) Date of Patent: Jun. 11, 2013

(54) INTRALUMINAL DEVICE WITH A COATING CONTAINING SYNTHETIC FISH OIL AND A THERAPEUTIC AGENT

(75) Inventors: Maria Dhondt, Nazareth (BE); Ivan De Scheerder, Herent (BE); Pierre Jacobs, Gooik (BE); Johan Martens, Huldenberg (BE)

(73) Assignee: Atrium Medical Corporation, Hudson, NH (US)

( * ) Notice: Subject to any disclaimer, the term of this patent is extended or adjusted under 35 U.S.C. 154(b) by 1410 days.

(21) Appl. No.: 10/494,892

(22) PCT Filed: Nov. 8, 2002

(86) PCT No.: PCT/BE02/00166
§ 371 (c)(1),
(2), (4) Date: Mar. 25, 2005

(87) PCT Pub. No.: WO03/039612
PCT Pub. Date: May 15, 2003

(65) Prior Publication Data
US 2005/0158361 A1 Jul. 21, 2005

(30) Foreign Application Priority Data

Nov. 8, 2001 (EP) .................................. 01870237
Mar. 28, 2002 (EP) .................................. 02447048
Apr. 26, 2002 (EP) .................................. 02447075

(51) Int. Cl.
*A61F 2/00* (2006.01)
*A61F 2/06* (2006.01)
(52) U.S. Cl.
USPC .......... 424/423; 623/1.1; 623/1.42; 623/1.43; 623/1.46; 623/1.49
(58) Field of Classification Search
None
See application file for complete search history.

(56) References Cited

U.S. PATENT DOCUMENTS

| | | | |
|---|---|---|---|
| 4,323,547 A | 4/1982 | Knust et al. | |
| 4,711,902 A | 12/1987 | Serno | |
| 4,733,665 A | 3/1988 | Palmaz | |
| 4,814,329 A | 3/1989 | Harsanyi et al. | |
| 4,846,844 A | 7/1989 | De Leon et al. | |
| 4,847,301 A | 7/1989 | Murray | |
| 4,894,231 A | 1/1990 | Moreau et al. | |
| 4,952,419 A | 8/1990 | De Leon et al. | |
| 5,118,493 A | 6/1992 | Kelley et al. | |
| 5,151,272 A | 9/1992 | Engstrom et al. | |
| 5,283,257 A * | 2/1994 | Gregory et al. ............... | 514/458 |
| 5,371,109 A | 12/1994 | Engstrom et al. | |
| 5,464,650 A | 11/1995 | Berg et al. | |
| 5,509,899 A | 4/1996 | Fan et al. | |
| 5,573,781 A | 11/1996 | Brown et al. | |
| 5,579,149 A | 11/1996 | Moret et al. | |
| 5,591,230 A | 1/1997 | Horn et al. | |
| 5,603,721 A | 2/1997 | Lau et al. | |
| 5,605,696 A * | 2/1997 | Eury et al. ..................... | 424/423 |
| 5,637,113 A | 6/1997 | Tartaglia et al. | |
| 5,641,767 A * | 6/1997 | Wess et al. .................... | 514/172 |
| 5,700,286 A | 12/1997 | Tartaglia et al. | |
| 5,753,259 A | 5/1998 | Engstrom et al. | |
| 5,843,172 A * | 12/1998 | Yan .............................. | 623/1.42 |
| 5,874,470 A | 2/1999 | Nehne et al. | |
| 5,897,911 A * | 4/1999 | Loeffler ....................... | 427/2.25 |
| 5,902,266 A | 5/1999 | Leone et al. | |
| 5,906,831 A | 5/1999 | Larsson et al. | |
| 5,955,502 A | 9/1999 | Hansen et al. | |
| 6,004,549 A | 12/1999 | Reichert et al. | |
| 6,005,004 A | 12/1999 | Katz et al. | |
| 6,033,436 A * | 3/2000 | Steinke et al. ............... | 623/1.15 |
| 6,077,698 A | 6/2000 | Swan et al. | |
| 6,083,950 A | 7/2000 | Anand et al. | |
| 6,090,809 A | 7/2000 | Anand et al. | |
| 6,117,911 A | 9/2000 | Grainger et al. | |
| 6,146,358 A | 11/2000 | Rowe | |
| 6,193,746 B1 | 2/2001 | Strecker | |
| 6,197,357 B1 | 3/2001 | Lawton et al. | |
| 6,206,916 B1 | 3/2001 | Furst | |

(Continued)

FOREIGN PATENT DOCUMENTS

| | | |
|---|---|---|
| DE | 19916086 | 10/1999 |
| EP | 0623354 | 11/1994 |

(Continued)

OTHER PUBLICATIONS

Wanasundara et al. Effect of processing on constiuents and oxidative stability of marine oils, Journal of Food Lipids 5, 1998, p. 29-41.*
CRC Handbook of Chemistry and Physics, 89th Edition, 2008-2009, Composition and Properties of Common Oils and Fats, pp. 7-9 to 7-13.*
Ali 1994. Handbook of Industrial Chemistry: Organic Chemicals. Chapter 4. Edible Fats, oils, and Waxes. pp. 85-121.*
Rietjens et al 2002. The pro-oxidant chemistry of the natural antioxidants vitamin C, vitamin E, carotenoids, and flavonoids. Environmental Toxicology and Pharmacology, vol. 11:321-333.*
Luostarinen et al 1995. Vitamin E supplementation counteracts the fish oil induced increase of blood glucose in humans. Nutrition Research, vol. 15(7):953-968.*
Pilz and Marz 2008. Free fatty acids as a cardiovasulcar risk factor. Clin Chem Lab Med, vol. 46(4):429-434.*

(Continued)

*Primary Examiner* — Carlos Azpuru
*Assistant Examiner* — Casey Hagopian
(74) *Attorney, Agent, or Firm* — Sean D. Detweiler, Esq.; Morse, Barnes-Brown & Pendleton, P.C.

(57) ABSTRACT

The invention relates to an intraluminal device, in particular an intraluminal prosthesis, shunt, catheter or local drug delivery device. In order to increase the bio-compatibility of this device, it is provided with at least one coating. The coating contains a therapeutic agent which is comprised in a matrix that sticks to the intraluminal device. Instead of being formed by a little bio-compatible polymer, the matrix is formed by a bio-compatible oil or fat, such as cod-liver oil or olive oil. Preferably, the bio-compatible oil or fat further comprises alfa-tocopherol.

27 Claims, No Drawings

U.S. PATENT DOCUMENTS

| | | |
|---|---|---|
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,811 B1 | 6/2001 | Horrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,306,438 B1 * | 10/2001 | Oshlack et al. ............ 424/468 |
| 6,331,568 B1 | 12/2001 | Horrobin |
| 6,358,556 B1 | 3/2002 | Ding et al. |
| 6,364,893 B1 | 4/2002 | Sahatjian et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,491,938 B2 | 12/2002 | Kunz |
| 6,503,556 B2 | 1/2003 | Harish et al. |
| 6,527,801 B1 | 3/2003 | Dutta |
| 6,569,441 B2 | 5/2003 | Kunz et al. |
| 6,610,035 B2 | 8/2003 | Yang et al. |
| 6,641,611 B2 | 11/2003 | Jayaraman |
| 6,645,547 B1 | 11/2003 | Shekalim et al. |
| 6,663,880 B1 | 12/2003 | Roorda et al. |
| 6,670,355 B2 | 12/2003 | Azrolan et al. |
| 6,677,342 B2 | 1/2004 | Wolff et al. |
| 6,730,064 B2 | 5/2004 | Ragheb et al. |
| 6,764,509 B2 | 7/2004 | Chinn et al. |
| 6,776,796 B2 | 8/2004 | Falotico et al. |
| 6,833,004 B2 | 12/2004 | Ishii et al. |
| 6,899,729 B1 | 5/2005 | Cox et al. |
| 6,918,927 B2 | 7/2005 | Bates et al. |
| 7,323,189 B2 * | 1/2008 | Pathak ............ 424/423 |
| 2001/0022988 A1 | 9/2001 | Schwarz et al. |
| 2001/0025196 A1 | 9/2001 | Chinn et al. |
| 2001/0027299 A1 | 10/2001 | Yang et al. |
| 2002/0007209 A1 | 1/2002 | Scheerder et al. |
| 2002/0032414 A1 | 3/2002 | Ragheb et al. |
| 2002/0098278 A1 | 7/2002 | Bates et al. |
| 2002/0120333 A1 | 8/2002 | Keogh et al. |
| 2002/0122877 A1 | 9/2002 | Harish et al. |
| 2002/0127327 A1 | 9/2002 | Schwarz et al. |
| 2003/0003125 A1 | 1/2003 | Nathan et al. |
| 2003/0004564 A1 | 1/2003 | Elkins et al. |
| 2003/0033004 A1 | 2/2003 | Ishii et al. |
| 2003/0065292 A1 | 4/2003 | Darouiche et al. |
| 2003/0069632 A1 | 4/2003 | De Scheerder et al. |
| 2003/0072784 A1 | 4/2003 | Williams |
| 2003/0077310 A1 | 4/2003 | Pathak et al. |
| 2003/0083740 A1 | 5/2003 | Pathak |
| 2003/0086958 A1 | 5/2003 | Arnold et al. |
| 2003/0175408 A1 | 9/2003 | Timm et al. |
| 2003/0176915 A1 | 9/2003 | Wright et al. |
| 2003/0181975 A1 * | 9/2003 | Ishii et al. ............ 623/1.42 |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2004/0014810 A1 | 1/2004 | Horrobin |
| 2004/0039441 A1 | 2/2004 | Rowland et al. |
| 2004/0137066 A1 | 7/2004 | Jayaraman |
| 2004/0167572 A1 | 8/2004 | Roth et al. |
| 2004/0170685 A1 | 9/2004 | Carpenter et al. |
| 2004/0224003 A1 | 11/2004 | Schultz |
| 2004/0230176 A1 | 11/2004 | Shanahan et al. |
| 2005/0159809 A1 | 7/2005 | Hezi-Yamit et al. |
| 2005/0182485 A1 | 8/2005 | Falotico et al. |
| 2005/0187376 A1 | 8/2005 | Pacetti |
| 2005/0232971 A1 | 10/2005 | Hossainy et al. |
| 2005/0249775 A1 | 11/2005 | Falotico et al. |
| 2006/0008501 A1 | 1/2006 | Dhont et al. |
| 2010/0209473 A1 | 8/2010 | Dhont et al. |

FOREIGN PATENT DOCUMENTS

| | | |
|---|---|---|
| EP | 0623354 B1 | 11/1994 |
| EP | 0730864 B1 | 9/1996 |
| EP | 0790822 B1 | 8/1997 |
| EP | 0873133 B1 | 10/1998 |
| EP | 0917561 B1 | 5/1999 |
| EP | 0950386 | 10/1999 |
| EP | 1132058 | 9/2001 |
| EP | 1140243 B1 | 10/2001 |
| EP | 1870237.3 | 11/2001 |
| EP | 1181943 A1 | 2/2002 |
| EP | 2447048.6 | 3/2002 |
| EP | 2447075.9 | 4/2002 |
| EP | 1270024 A1 | 1/2003 |
| EP | 1273314 A1 | 1/2003 |
| EP | 1364628 A1 | 11/2003 |
| EP | 1557183 A1 | 7/2005 |
| EP | 1576970 | 9/2005 |
| EP | 2201965 | 6/2010 |
| GB | 2363572 | 1/2002 |
| JP | 49-50124 | 5/1974 |
| JP | 61-291520 | 12/1986 |
| JP | 1-175864 | 7/1989 |
| JP | 1-503296 | 9/1989 |
| JP | 8-224297 | 9/1996 |
| JP | 2001-10958 | 1/2001 |
| RU | 2125887 | 2/1999 |
| SU | 1297865 | 3/1987 |
| WO | WO-87/06463 | 11/1987 |
| WO | WO-90/01969 A1 | 3/1990 |
| WO | WO-95/17901 A1 | 7/1995 |
| WO | WO-95/26715 A2 | 10/1995 |
| WO | WO-96/18417 A1 | 6/1996 |
| WO | WO-97/02042 A1 | 1/1997 |
| WO | WO-97/09367 A1 | 3/1997 |
| WO | WO-97/13528 A1 | 4/1997 |
| WO | WO-98/23228 | 6/1998 |
| WO | WO-98/30206 A1 | 7/1998 |
| WO | WO-98/54275 | 12/1998 |
| WO | WO-98/54275 A3 | 12/1998 |
| WO | WO-99/40874 | 8/1999 |
| WO | WO-00/40236 A1 | 7/2000 |
| WO | WO-00/40278 A1 | 7/2000 |
| WO | WO-00/53212 A1 | 9/2000 |
| WO | WO-00/62830 | 10/2000 |
| WO | WO-00/62830 A2 | 10/2000 |
| WO | WO 0062830 A2 * | 10/2000 |
| WO | WO-01/24866 A1 | 4/2001 |
| WO | WO-01/26585 A1 | 4/2001 |
| WO | WO-01/45763 A1 | 6/2001 |
| WO | WO-01/66036 A2 | 9/2001 |
| WO | WO-01/76649 A1 | 10/2001 |
| WO | WO-02/49535 A2 | 6/2002 |
| WO | WO-02/100455 A2 | 12/2002 |
| WO | WO-03/000308 A1 | 1/2003 |
| WO | WO-03/015748 A2 | 2/2003 |
| WO | WO-03/028622 A2 | 4/2003 |
| WO | WO-03/037397 A2 | 5/2003 |
| WO | WO-03/037398 A2 | 5/2003 |
| WO | WO-03/039612 A1 | 5/2003 |
| WO | WO-03/041756 A1 | 5/2003 |
| WO | WO-03/070125 A1 | 8/2003 |
| WO | WO-03/092741 A1 | 11/2003 |
| WO | WO-2004/004598 A2 | 1/2004 |
| WO | WO-2004/006976 A1 | 1/2004 |
| WO | WO-2004/006978 A1 | 1/2004 |
| WO | WO-2005/000165 A1 | 1/2005 |
| WO | WO-2005/016400 A1 | 2/2005 |
| WO | WO-2005/053767 A1 | 6/2005 |

OTHER PUBLICATIONS

Sigma-Aldrich. Polyhydroxy compounds web page, captured May 28, 2009.*

Luostarinen et al 1995. Vitamin E supplementation counteracts the fish oil induced increase of blood glucose in humans. Nutrition Research, vol. 15(7):953-968.*

The Lipid Handbook, Second Edition, 1994. Tocopherols, pp. 129-131.*

Kaczynski, Jason, Natural Omega3 Fish Oil Supplements—How to Avoid Synthetic Fish Oils, accessed online at http://ezinearticles.com/?Natural-Omega3-Fish-Oil-Supplements---How-to-Avoid-Synthetic-Fish-Oils&id=2460278, Jun. 10, 2009.*

European Communication for Application No. 07112611.4-2107, dated Nov. 30, 2007.

A paper entitled, "Evaluation of the Biocompatibility and Drug Delivery Biological Oil Based Stent Coatings," by Li, Shengqiao of the Katholieke Universiteit Leuven.

Camurus, "In our endeavors to create the unique, we start with the best. Your product."

Drummond, Calum J. et al, "Surfactant self-assembly objects as novel drug delivery vehicles," *Current Opinion in Colloid & Interface Science*, vol. 4:449-456 (2000).

Engström, Sven, "Drug Delivery from Cubic and Other Lipid-Water Phases," *Lipid Technology*, vol. 2(2):42-45 (1990).

Hwang, Chao-Wei et al, "Physiological Transport Forces Govern Drug Distribution for Stent-Based Delivery," *Circulation*, vol. 104:600-605 (2001).

Oberhoff, Martin et al, "Local and Systemic Delivery of Low Molecular Weight Heparin Following PTCA: Acute Results and 6-Month Follow-Up of the Initial Clinical Experience With the Porous Balloon (PILOT-Study)," *Catheterization and Cardiovascular Diagnosis*, vol. 44:267-274 (1998).

Salu, Koen J. et al, "Addition of cytochalasin D to a biocompatible oil stent coating inhibits intimal hyperplasia in a porcine coronary model," *Coronary Artery Disease*, vol. 545-555 (2003).

Scheller, Bruno et al, "Addition of Paclitaxel to Contrast Media Prevents Restenosis After Coronary Stent Implantation," *Journal of the American College of Cardiology*, vol. 47(8):1415-1420 (2003).

De Scheerder et al., "Local Angiopeptin Delivery Using Coated Stents Reduces Neointimal Proliferation in Overstretched Porcine Coronary Arteries," J. Invasive Cardiol., 8:215-222 (1995).

De Scheerder et al., "Biocompatibility of polymer-coated oversized metallic stents implanted in normal porcine coronary arteries," Atherosclerosis, 114(1):105-114 (1995).

De Scheerder et al., "Experimental Study of Thrombogenicity and Foreign Body Reaction Induced by Heparin-Coated Coronary Stents," Circulation, 95:1549-1553 (1997).

Schwartz et al., "Restenosis and the Proportional Neointimal Response to Coronary Artery Injury: Results in a Porcine Model." J. Am. Coll. Cardiol., 19:267-274 (1992).

Van der Giessen et al., "Marked Inflammatory Sequelae to Implantation of Biodegradable and Nonbiodegradable Polymers in Porcine Coronary Arteries," Circulation, 94(7):1690-1697 (1996).

Luostarinen et al., "Vitamin E Supplementation Counteracts the Fish Oil Induced Increase of Blood Glucose in Humans," Nutritional Research, 1995, 15(8):953-958.

International Search Report for International Application PCT/BE02/00166, dated Apr. 3, 2003.

European Search Report for Application EP 05012112, dated Jul. 5, 2005.

European Search Report for Application EP 10157210, dated May 20, 2010.

Non-Final Office Action for U.S. Appl. No. 11/140,811, mailed Sep. 15, 2008.

Final Office Action for U.S. Appl. No. 11/140,811, mailed Nov. 25, 2009.

Non-Final Office Action for U.S. Appl. No. 12/767,289, mailed Aug. 19, 2011.

* cited by examiner

INTRALUMINAL DEVICE WITH A COATING CONTAINING SYNTHETIC FISH OIL AND A THERAPEUTIC AGENT

The present invention relates to an intraluminal device, in particular an intraluminal prosthesis, shunt, catheter or local drug delivery device, provided with at least one coating containing a therapeutic agent comprised in a matrix which sticks to the intraluminal device.

Several trials with systematically (oral or intravenous) administered anti-restenotic therapeutic agents after dilatation of narrowed lumina (for example of a coronary arterial atherosclerotic narrowing) failed in consequence of a too limited therapeutic agent concentration on the place where the therapeutic agent has to act and due to the systemic therapeutic agent's side effects when higher doses are administered. For this reason therapeutic agents were applied locally, at the place of the organ to be treated. For example in the treatment of coronary stenoses using special catheters, therapeutic agents were injected into the vessel wall. Disadvantages of this approach are the limited efficiency of the so-called local treatment (less than 5% of the administered therapeutic agent reaches the target organ) and the increased damage to the target organ due to the local drug administration.

Another method is the coverage of an endoluminal prosthesis with a polymer coating and the impregnation of the polymer with a therapeutic agent (EP-A-0623354). The disadvantages of this method are the limited drug capacity of the coating and the too fast release of the therapeutic agent because of the large contact area. Furthermore, polymers need a quite aggressive polymerisation step that can result in inactivation of the therapeutic agent and most polymers are not very bio-compatible and induce a foreign body inflammatory response, resulting in even more hyperplasia and restenosis.

The object of the present invention is therefore to provide a new intraluminal device which is provided with a coating which does not need an aggressive polymerisation step, which is bio-compatible and which enables to obtain a sustained local release of the therapeutic agent.

To achieve this object, the intraluminal device according to the invention is characterised in that the matrix which comprises the therapeutic agent is formed by a bio-compatible oil or fat.

It has been found rather surprisingly that an oil or fat adheres sufficiently strongly to the intraluminal device so that most of the coating remains on the intraluminal device when inserting it in the lumen. The oil or fat matrix further slows down the release of the therapeutic agent once inserted in the body lumen. Due to the selection of a bio-compatible oil or fat, the coating reduces the foreign body inflammatory response induced by the intraluminal device. A further advantage of an oil or fat coating is that it has a lubricating effect so that no further lubricants have to be used which may reduce the bio-compatibility of the intraluminal device.

By bio-compatible oil or fat is meant is the present specification that the oil or fat does not have any intolerable adverse effect on the lumen structure wherein the intraluminal device is to be applied.

The term "oil or fat" is further used to designated substances which have the physical characteristics of an oil or a fat, a fat differing only in one respect from an oil, a fat being solid at room temperature whilst an oil is liquid at room temperature. In liquid state, i.e. at a sufficiently high temperature, oils and fats have a viscous consistency and a characteristic unctuous feel. They are moreover lighter than water and insoluble in it.

Due to their fatty, viscous consistency, fats and oils are able to stick sufficiently strongly to the intraluminal device. Moreover, since they are not soluble in water, they are able to provide for a prolonged release of the therapeutic agent in the body lumen.

As oil or fat different products can be used. First of all, although some mineral oils may be bio-compatible, animal or vegetable oils are suitable, in particular edible oils such as fish oil, olive oil, linseed oil, sunflower oil, corn oil and/or palm or palmnut oil. Good effects have been demonstrated experimentally for cod-liver oil and olive oil. The oils do not need to be used in their natural form but the chemical structure thereof can be modified. The natural, biological oils can in particular be hydrogenated (preferably only partially so that they still contain unsaturated fatty acids) resulting in an increased melting point. Further, it is possible to produce synthetic oils or fats having a composition similar to the composition of the natural oils or to the composition of particular components thereof, in particular triglycerides.

In the above mentioned preferred embodiment, the oils comprise triglycerides composed of glycerol and one or more fatty acids. Preferably, they comprise more than 20% by weight, and most preferably more than 70% by weight of triglycerides. These amounts are either present in the natural oils or they can be achieved by adding triglycerides or by further purifying the oils. In other embodiments of the present invention, it is however possible to substitute other trihydroxy or polyhydroxy compounds for the glycerol. A special preference is given to cod-liver oil which is purified so that it contains more than 90% of triglycerides.

The oils or fats may also contain free fatty acids (having a free —COOH group) but this preferably in an amount of less than 50% by weight and more preferably only in minor proportions, e.g. less than about 10% by weight free fatty acids. The oils or fats can further be composed of, or may comprise other fatty acid derivatives, in particular methyl or ethyl esters of fatty acids.

An example of a further "oily" or "fatty" substance which can be used as bio-compatible oil or fat is alfa-tocopherol and/or a derivative thereof such as alfa-tocopherol acetate. The alfa-tocopherol and/or a derivative thereof may either be a component of the oil or fat or the oil or fat may consist substantially entirely of this compound.

As disclosed already in EP-A-0 623 354 tocopherol (vitamin E) is a therapeutic agent. In general, in accordance with the present invention, the oil or fat forming the matrix which sticks to the intraluminal device may thus be formed partially or completely by the therapeutic agent when this therapeutic agent is an oil or a fat. Of course one or more further therapeutic agents can be incorporated in the thus formed oil or fat matrix.

The present inventors have found that alfa-tocopherol and/or derivatives thereof are preferably used in combination with an oil or fat comprising fatty acids and/or derivatives thereof, in particular one or more triglycerides. They have found more particularly that coatings containing this combination showed a very good bio-compatibility to vascular tissue. The observed effects on the decrease on the inflammation score, and especially on the decrease of the area stenosis and of the neointimal hyperplasia, indicating the occurrence of synergetic effects. The alfa-tocopherol and/or the derivatives thereof are preferably mixed with the oil or fat comprising fatty acids and/or derivatives thereof to achieve such synergetic effects but a top coat of the alfa-tocopherol and/or the derivatives thereof on a first oil or fat coating appeared to provide also good results. Such a top coat comprises preferably said alfa-tocopherol and/or said derivative thereof in an amount of at least 90% by weight and most preferably in an amount of at least 95% by weight. When being a component of the oil or fat of the coating, this oil or fat comprises the alfa-tocopherol, and/or the derivative thereof, preferably in an amount of between 20 and 80% by weight, more preferably in an amount of between 30 and 70% by weight.

Instead of being a component of the oil or fat, the therapeutic agent may also be chemically bonded to the oil or fat by any chemical bonding technique. When the oil or fat comprises for example triglycerides, the therapeutic agent may for example be chemically bound to the fatty acid groups or to the glycerol group. On the other hand, the fatty acid groups themselves may be formed by fatty acids which may be therapeutic agents. Such fatty acids are in particular unsaturated fatty acids, more particularly omega-3 fatty acids. In view of their therapeutic effect, the fatty acids are preferably formed by more than 5%, more preferably by more than 10% and most preferably by more than 15% by weight of unsaturated fatty acids. Most preferably these unsaturated fatty acids comprise eicosapantaenoic acid (EPA) and optionally decosahexaenoic acid (DHA). Experiments have shown in particular for cod-liver oil and for olive oil that a coating consisting only of such an oil, i.e. without added therapeutic agents, has already a beneficial effect on the healing response resulting in an improved patency of the prosthesis. The beneficial effect of bio-compatible oils like cod-liver oil and olive oil may be explained by their anti-oxidant and anti-inflammatory effect, in particular the anti-oxidant effect of their unsaturated fatty acids. This anti-oxidant effect can be increased by added or naturally present vitamin E or derivatives thereof having an anti-oxidant effect (for example when the oil or fat has been hydrogenated partially). Furthermore bio-compatible oils inhibit smooth muscle cell proliferation in cell culture experiments.

In the device according to the present invention, the therapeutic agent may also be mixed with the oil or fat. When soluble in the oil or fat, the therapeutic agent can be dissolved therein or, when it is not soluble in the oil or fat, it can be dispersed therein, more particularly emulsified or suspended depending on the fact whether the therapeutic agent is a liquid or a solid.

The therapeutic agent may be selected from the group consisting of vinblastine, sirolimus, mitoxantrone, tacrolimus, paclitaxel, cytochalasin, latrunculin, and everolimus, a particular preference being given to everolimus. It can also be selected from the group consisting of deferoxamine, geldanamycin, nigericin, penitrem, paxilline, verruculogen, KT5720, KT5823, Anisomycin, chelerythrine chloride, genistein, parthenolide, trichostatin A, T2 toxin, Zearalenone, Interferon, epithalon-D, Ca-ionophore, 4 bromo Ca Ionophore, Aflatoxins, aphidicolin, brefeldin A, cerulenin, chromomycin A3, citrinin, cyclopiazonic acid, forsokolin, fumagillin, fumonisins B1, B2, hypericin, K252, mycophenolic acid, ochratoxin A, and oligomycin or further from the group consisting of mycophenolic acid, mycophenolate mofetil, mizoribine, methylprednisolone, dexamethasone and other corticosteroids, CERTICAN® (everolimus), triptolide, methotrexate, benidipine, ascomycin, wortmannin, LY 294002, Camptothecin, Topotecan, hydroxyurea, cyclophosphamide, cyclosporin, daclizumab, azathioprine, gemcitabine, and derivatives and analogues thereof. As therapeutic agents genes, coding for certain substances (proteins), having either anti-thrombotic and/or anti-restenotic action, can be used as well.

The therapeutic agent may have different effects and may in this respect be selected amongst immunosuppressants, anti-inflammatories, anti-proliferatives, anti-migratory agents, anti-fibrotic agents, proapoptotics, calcium channel blockers, anti-neoplastics, antibodies, anti-thrombotics, antiplatelet agents, IIb/IIIa blockers, antiviral agents, anti-cancer agents, chemotherapeutics, thrombolytics, vasodilators, antibiotics, growth factor antagonists, free radical scavengers, radiopaque agents, anti-angiogenesis agents, angiogenesis drugs, cyclooxygenase inhibitors, phosphodiesterase inhibitors, cytokine inhibitors, nitrogen oxide donors, and cytokine activators.

The coating provided on the intraluminal device in accordance with the present invention may comprise other substances in addition to the therapeutic agent and the oil or fat. It is for example possible to add some substances, in particular some natural or synthetic polymeric substances, binders, thickening agents, etc. to the coating in order to stabilise it. The amount of such substances is however preferably kept below 30%, more preferably below 85% and most preferably below 95% by weight in order to maintain the improved bio-compatibility of the oil or fat coating as much as possible. This means that the coating comprises preferably at least 70% by weight, more preferably at least 85% by weight and most preferably at least 95% by weight of the oil or fat and the therapeutic agent. The oil or fat content of the coating is preferably at least 50% by weight, more preferably at least 70% by weight, and most preferably at least 80% by weight, a particular preference being given to an oil or fat content of at least 90% by weight.

In order to control or tailor the release of the therapeutic agent out of the coating, a top coat can be applied on top of this coating, in particular a top coat of the same or a different bio-compatible oil or fat. The rate at which the therapeutic agent is delivered can further be controlled by the ratio of therapeutic agent to oil or fat in the coating or by providing multiple coatings with varying drug concentrations. In the device according to the present invention the release of therapeutic agent can further be controlled by the selection of an appropriate bio-compatible oil or fat having a certain stability level and melting point.

The oil or fat has preferably a melting point lower than 100° C. and more preferably lower than 80° C. so that the therapeutic agent can be mixed with the oil or fat in the molten state thereof without having a deleterious effect on the therapeutic agent. The melting temperature is preferably even lower than 60° C., more preferably lower than 40° C., so that a mixture can be made of the therapeutic agent, the oil or fat in its molten state and a volatile solvent such a ethanol.

In view of the fact that the release of the therapeutic agent may be too slow from the oil or fat matrix in the solid state thereof, the melting point of the oil or fat is preferably lower or equal to 37° C. so that the oil or fat will be in the molten state once inserted in the body lumen.

The oil or fat may be an oil at room temperature. The above mentioned natural oils are for example liquid at room temperature, except palm oil and palm nut oil. Linseed oil, sunflower oil, corn oil, olive oil and cod-liver oil have a melting point lower or equal to about 0° C. Experiments have shown that even with such a low melting point, these oils are able to stick sufficiently strongly to the intraluminal device. However, in order to have a more stable coating, these unsaturated oils can be further stabilised by a partial hydrogenation resulting in an increase of their melting point. The melting point can be raised to a melting point higher than 10, 15, 20 or 30° C. depending on the desired stability (viscosity) of the oil or fat and the release properties thereof.

When use is made of a chemically hardened oil or fat which still comprises unsaturated fatty acid chains, the hardened oil or fat is preferably free of trans isomers of unsaturated fatty acid chains. Natural oils are normally free of such trans isomers. During the usual hardening processes, trans isomers are however formed. Since such trans isomers may have negative effects, they are preferably removed, for example in accordance with the technique described in WO 98/54275.

The present invention also relates to a method for providing an intraluminal device, in particular an intraluminal prosthesis, shunt, catheter or local drug delivery device, with at least one coating containing a therapeutic agent comprised in a matrix which sticks to the intraluminal device. In accordance with the invention, the matrix is formed by a bio-compatible oil or fat, which comprises said therapeutic agent, and which is applied in a flowable state onto the device.

When the oil or fat has a sufficiently low viscosity (optionally after heating), it can be applied in a molten state onto the device. Usually, use is however preferably made of a solvent which is mixed with the oil or fat before applying the oil or fat onto the device and, after having applied the mixture of solvent and oil or fat onto the device, the solvent is allowed to evaporate. The solvent is normally an organic solvent, in particular an alcohol such as ethanol.

When the oil or fat is soluble in the solvent, a solution of the oil or fat in the solvent can first be made after which the therapeutic agent, when not yet comprised in the oil or fat, can be added. When the oil or fat is not soluble, a homogeneous mixture is first made, in particular an emulsion. Alternatively, the therapeutic agent can first be dissolved or dispersed in the solvent before mixing it with the oil or fat.

A typical method according to a preferred embodiment of the present invention comprises the following steps:
a) Cleaning, degreasing and drying of the prosthesis
b) Dipping of the prosthesis in an deoxidative solution and airdrying it
c) Making an emulsion or solution of the bio-compatible oil or fat and a solvent, preferably in a liquid state of the oil or fat
d) In this emulsion/solution a therapeutic agent is dissolved when the oil or fat did not yet contain a therapeutic agent or an additional therapeutic agent is dissolved when the oil or fat did already contain a therapeutic agent. The therapeutic substance needs only to be dispersed throughout the solvent/oil emulsion or solution so that it may be either in a true solution with the solvent/oil emulsion or solution or dispersed in fine particles in the solvent/oil emulsion or solution.
e) Stirring of the obtained solution until achievement of a homogenous mixture/solution
f) Applying to the prosthesis body of the therapeutic agent containing oil/solvent emulsion or solution using dipcoating or spraycoating or any other coating method
g) Airdry till the solvent is evaporated.
h) Optionally repeat the previous steps multiple times, eventually using different therapeutic agents.
i) Further airdry the prosthesis in a sterile laminar flow.

Prior to step c, a therapeutic agent could already be added to the solvent or to the oil or fat. The oil or fat could for example be enriched with EPA and optionally DHA. It is also possible to add alfa-tocopherol and/or a derivative thereof to the oil or fat. Moreover, an oil or fat can be selected which comprises already groups which are therapeutically active, such as unsaturated fatty acid groups, or a therapeutic agent can be bonded to the oil or fat using any chemical bonding technique. When the oil or fat is already provided in this way with a therapeutic agent, it is not necessary any more to add a therapeutic agent although it is still possible to add further therapeutic agents. This is for example the case when the oil is formed by alfa-tocopherol or a derivative thereof or when the oil comprises alfa-tocopherol or a derivative thereof.

After drying a topcoat, consisting of a bio-compatible oil or fat, in particular a natureal edible oil or alfa-tocopherol (or an derivative thereof) or a combination thereof can be using dipcoating, spraycoating or any other coating method.

After drying, the obtained coated prosthesis can be used as such or further dried and sterilised. Light-protection of the obtained coated prosthesis is advisable to maintain the bio-compatible characteristics when stored.

The inclusion of a bio-compatible, in particular a biological oil or fat in intimate contact with a drug covering the prosthesis allows the drug to be retained in the prosthesis in a resilient matrix during expansion of the prosthesis and also slows the administration of drug following implantation. Furthermore, depending on the melting point of the biological oil used the oil can become a fat, retaining the drug and resulting in a more stable surface coating. Furthermore by addition of certain chemical substances (bicarbonate) or by hydrogenation the coating can be further stabilised resulting in a very stable drug containing coating. The method of the invention can be used whether the prosthesis has a metallic or polymeric surface. The method is also an extremely simple one since it can be effected by simply immersing the prosthesis into the solution (emulsion) or by spraying the solution (emulsion) onto the prosthesis. The amount of drug to be included onto the prosthesis can be readily controlled by using different drug concentrations and or different coating application methods. The rate at which the drug is delivered can be controlled by the selection of an appropriate bio-compatible oil or fat at a certain stability level and melting point and by the ratio of drug to oil in the solution. The release rate can be further controlled by using additional barrier coatings or multiple layers of coating with varying drug concentrations. Furthermore this system allows the use of different therapeutic agents. In operation, prosthesis made according to the present invention can deliver drugs to a body lumen by introducing the prosthesis transluminally into a selected portion of the body lumen and radially expanding the prosthesis into contact with the body lumen. The transluminal delivery can be accomplished by a catheter designed for the delivery of the prostheses and the radial expansion can be accomplished by balloon expansion of the prosthesis, by self-expansion of the prosthesis or a combination of self-expansion and balloon expansion.

Thus the present invention provides a prosthesis which may be delivered and expanded in a selected body lumen or conduit without losing a therapeutically significant amount of a drug or gene applied thereto. It also provides a drug or gene containing prosthesis which allows for a sustained release of the drug or gene to luminal or conduit tissue.

The underlying structure of the prosthesis used according to the invention can be virtually any prosthesis design, for example of the self-expanding type or of the balloon expandable type, and of metal or polymeric material. Thus metal prosthesis designs such as those disclosed in U.S. Pat. No. 4,733,665 (Palmaz) and U.S. Pat. No. 5,603,721 (Lau) could be used in the present invention. Also prosthesis with special surface treatments or special designs to optimise local drug delivery are especially suitable for this invention (for example: DE199 16 086 A1, EP 0 950 386 A2, EP 1 132 058 A1, WO 01/66036 A2, WO 98/23228, U.S. Pat. No. 5,902, 266, U.S. Pat. No. 5,843,172, . . . ). The surface of the prosthesis could in particular be provided with perforating holes or pits which can be filled with the coating material to increase the load of therapeutic agent and/or to slow down the release. After having applied the coating, the surface of the prosthesis next to the holes or pits can be wiped off or cleaned to remove the coating material. The present invention therefore does not only embrace continuous coatings covering the entire prosthesis but also discontinuous local coatings or combinations of local coatings and continuous top coatings applied thereover. The coating further does not need to be applied on the surface of the prosthesis. When using for example porous prostheses, the coating may be located within the pores of the prosthesis. The prosthesis could be made of virtually any bio-compatible material having physical properties suitable for the design. For example, tantalum, nitinol and stainless steel have been proven suitable for many such designs and could be used in the present invention. Also, prostheses made of biostable or bioabsorbable polymers such as poly(ethylene terephthalate), polyacetal, poly(lactic acid), poly(ethylene oxide)/poly(butylene terephthalate) copolymer could be used in the present invention. Although the prosthesis surface should be clean and free from contaminants that may be introduced during manufacturing, the prosthesis surface requires no particular surface treatment in order to retain the coating applied in the present invention.

The oil or fat chosen should be bio-compatible and minimise irritation to the vessel wall when the prosthesis is implanted. The ratio of therapeutic substance to the oil/solvent emulsion in the solution will depend on the efficacy of the oil or fat in securing the therapeutic substance onto the prosthesis and the rate at which the coating is to release the therapeutic substance to the tissue of the blood vessel or body conduit. More oil or fat may be needed if it has relatively poor efficacy in retaining the therapeutic substance on the prosthesis and more oil may be needed in order to provide an elution matrix that limits the elution of a very soluble therapeutic substance. A wide ratio of therapeutic substance to oil/solvent emulsion could therefore be appropriate, in particular a weight ratio ranging from about 100:1 to 1:100.

EXPERIMENTAL WORK WITH THIS NEW COATING METHOD

The biological coatings are based upon:
1) biological dissolvable oils (fish oil, olive oil and other biological oils),
2) alfa tocoferol (Vit E oil solution) and mixtures of these components (50/50) either used in a single layer or used in multiple layers.

All coating solutions were shaken well until homogenous solutions were achieved.

Stent and Stent Coating

Balloon mounted stainless steel balloon-expandable coronary stents, 16 mm long, were used for these studies. The bare stents were sterile and dipped in a bicarbonate solution and air-dried, then dipcoated in the oil coating solution. The coated stents were air-dried or sterilized with ethylene oxide before implantation in porcine coronary arteries. The surface characteristics of the coated stents were examined by light and scanning electron microscopy (SEM).

Stent Implantation

Domestic cross bred pigs of both sexes, weighing 20-25 kg were used. They were fed with a standard natural grain diet without lipid or cholesterol supplementation throughout the study. All animals were treated and cared for in accordance with the Belgium National Institute of Health Guidelines for care and use of laboratory animals.

Acute Study

In this study control bare stents and oil coated stents (cod-liver oil (CLO), alfa-tocopherol oil solution (VIT E), CLO+VIT. E, in each group 5 stents) were randomly implanted in the coronary arteries of pigs. Pigs were sacrificed after 5 days to evaluate acute inflammatory response and thrombus formation.

Chronic Study

In this study control bare stents (n=16) and oil coated stents (CLO n=13, VIT E n=16, CLO+VIT E n=3) were implanted randomly in the coronary arteries of pigs. Pigs were sacrificed after 4 weeks to evaluate peri-strut inflammation and neointimal hyperplasia.

Surgical procedures and stent implantation in the coronary arteries were performed according to the method described by De Scheerder et al in "Local angiopeptin delivery using coated stents reduces neointimal proliferation in overstretched porcine coronary arteries." J. Inves. Cardiol. 8: 215-222; 1996, and in "Experimental study of thrombogenicity and foreign body reaction induced by heparin-coated coronary stents." Circulation 95: 1549-1553; 1997.

The guiding catheter was used as a reference to obtain an oversizing from 10 to 20%.

Tissue Processing for Histomorphometric Analysis

At 5 days or 4 weeks follow-up, the pigs were sacrificed and the stented coronary arteries were perfused with a 10% formalin solution at 80 mmHg. Artery segments were carefully dissected together with minimum a 1 cm vessel segment both proximal and distal to the stent. The segments were furthermore fixed in a 10% formalin solution. Each segment was cut into a proximal, middle and distal stent segment for histomorphometric analysis. Tissue specimens Were embedded in a cold-polymerizing resin (Technovit 7100, Heraus Kulzer GmbH, and Wehrheim, Germany). Sections, 5 microns thick, were cut with a rotary heavy duty microtome HM 360 (Microm, Walldorf, Germany) equipped with a hard metal knife, and stained with hematoxylin-eosin, masson's trichrome, elastic stain and a phosphotungstic acid hematoxylin stain. Light microscopic examination was performed blinded to the type of stent used. Injury of the arterial wall due to stent deployment was evaluated for each stent filament site and graded as described by Schwartz et al in "Restenosis and the proportional neointimal response to coronary artery injury: results in a porcine model." J. Am. Coll. Cardiol. 1992; 19(2): 267-74. Inflammatory reaction at every stent filament site was carefully examined searching for inflammatory cells, and scored as followed:

1=sparsely located histiolymphocytic infiltrate around the stent filament;
2=more densely located histiolymphocytic infiltrate covering the stent filament, but no foreign body granuloma or giant cells;
3=diffusely located inflammatory cells and/or giant cells, also invading the media.

Appearance of thrombus was evaluated for every stent filament on the phosphotungstic acid hematoxylin stained slides and graded as follows:

1=small thrombus adjacent to the stent filament;
2=more pronounced, covering the stent filament;
3=big thrombus resulting in an area stenosis of <50%;
4=big thrombus resulting in an area stenosis >50%.

The mean score was calculated as the sum of scores for each filament/number of filament present.

Morphometric analysis of the coronary segments harvested was performed on 3 slices (proximal, middle and distal stent part) by using a computerized morphometry program (Leitz CBA 8000). The areas of respectively the arterial lumen, the area inside the internal elastic lamina (IEL), and the area inside the external elastic lamina (EEL) were measured. Furthermore, the area stenosis (1-lumen area/IEL area) and the area of neointimal hyperplasia (IEL area−lumen area) were calculated.

Statistics

For comparison among different groups, the non-paired t-test is used. Data are presented as mean value±SD. A p value≦0.05 was considered as statistically significant.

4.19±0.93, P<0.001), but smaller than CLO+VIT E coated stents (5.17±1.19 vs 6.37±0.97, P<0.01). The neointimal hyperplasia of bare stents was comparable to VIT E stents, but higher than CLO coated stents (1.50±0.76 vs 1.25±0.61, P>0.05) Ind CLO+VIT E coated stents (1.50±0.76 vs 0.96±0.20, P<0.05).

TABLE 1

Histomorphometric response to the coated stents at 4 weeks follow-up

| Stents | n | Lumen Area (mm$^2$) | Hyperplasia (mm$^2$) | Area Stenosis (%) | Inflammation Score | Injury Score |
|---|---|---|---|---|---|---|
| Bare | 48 | 5.17 ± 1.19 | 1.50 ± 0.76 | 23 ± 13 | 1.10 ± 0.29 | 0.28 ± 0.39 |
| CLO | 39 | 5.59 ± 1.39 | 1.25 ± 0.61 | 19 ± 10 | 1.02 ± 0.07 | 0.19 ± 0.19 |
| VIT E | 48 | 4.19 ± 0.93*** | 1.60 ± 0.66 | 28 ± 12 | 1.00 ± 0.01* | 0.31 ± 0.26 |
| CLO + VIT E | 9 | 6.37 ± 0.97** | 0.96 ± 0.20* | 13 ± 3* | 1.00 ± 0.00* | 0.21 ± 0.16 |

Comparing to bare stents,
*P < 0.05,
**P < 0.01,
***P < 0.001

Results

SEM Images of the Coated Stents

The thickness of coating covering the stent filaments was 10 μm. The stent surface was smooth.

Histopathologic Findings (Table 1)

At 5 days follow-up, the bare and all CLO coated stents induced an identical histopathological response. The stent filaments showed a good alignment to the vascular wall. Internal elastic membrane was beneath the stent filaments and the media was compressed. Arterial injury induced by stent implantation was not significant different among the groups. A thin fibrin layer covering the stent filaments was observed. A few inflammatory cells trapped within a thrombotic meshwork covering the stent struts were observed. No significant different inflammatory score and thrombus score of CLO coated stents and bare stents were observed.

At 4 weeks follow-up, histopathological examination learned that the lumen surface of the CLO coated stents and bare stents were covered 6 completely with endothelial cells. A few inflammatory cells were found adjacent to the stent struts. A peri-strut inflammation score more than 2 was rare. The mean inflammation scores of all CLO coated stents were lower than the bare stents, although only VIT E coated stents showed a significantly decreased inflammation score (1.10±0.29 vs 1.00±0.01, P<0.05). Lacerated internal elastic lamina and media were observed. Comparing to bare stents, the arterial injury scores of CLO coated (0.28±0.39 vs 0.19±0.19, P>0.05) and CLO+VIT E coated stents (0.28±0.39 vs 0.21±0.16, P>0.05) were decreased.

Morphometry

At 4 weeks follow-up, the neointima of all CLO coated and bare stents was well organized which consisted of extracellular matrix and SMC's. The lumen area of bare stents was significantly larger than the VIT E coated stents (5.17±1.19 vs

CONCLUSION

All three coated and bare stents elicited a similar tissue response at 5 days follow-up. No additional inflammatory response and increased thrombus formation were observed with coated stents at that time point. At 4 weeks follow-up, all coated stents showed a mild inflammatory response. The inflammatory scores of coated stents were lower than the bare stents, especially using the VIT E coating. CLO and CLO+VIT E coated stents showed a decreased neointimal hyperplasia compared to the bare stents. The decreased lumen area of VIT E coated stents may be caused by smaller selected stented arteries as the neointimal hyperplasia of VIT E coated stents was comparable to bare stents.

In conclusion, all CLO, VIT E and CLO+VIT E coatings showed an excellent bio-compatibility to vascular tissue and could therefore serve as a vehicle for local drug delivery. The best results were obtained with the CLO+VIT E combination.

Olive Oil Coatings

In addition to the tests with cod-liver oil and vit. E oil, similar tests have been done with olive oil. The results of these tests are shown in Table 2. In this table it can be seen that, compared to the results for the bare stents given in Table 1, a coating consisting of only olive oil has beneficial effects on the lumen area, the neointimal hyperplasia and the area stenosis.

TABLE 2

Histomorphometric response to the olive oil coated stents at 4 weeks follow-up

| | Lum. a. | peri. | eq. dia. | IEL- a. | peri. | eq.dia. | EEL- a. | peri. | eq.dia. | IELa- Lum.a. | Dia.Ste. | Area Ste. | IEL Dia.- Lum.Dia. | EEL Dia.- Lum. Dia. |
|---|---|---|---|---|---|---|---|---|---|---|---|---|---|---|
| Prox | 5.59 | 9.05 | 2.67 | 6.94 | 10.08 | 2.97 | 8.74 | 11.08 | 3.34 | 1.35 | 10% | 19% | 0.30 | 0.67 |
| Mid | 4.82 | 8.86 | 2.48 | 6.05 | 9.40 | 2.78 | 7.82 | 10.59 | 3.15 | 1.23 | 11% | 20% | 0.30 | 0.67 |
| Dis | 5.42 | 8.73 | 2.63 | 6.33 | 9.48 | 2.84 | 7.69 | 10.22 | 3.13 | 0.91 | 7% | 14% | 0.21 | 0.50 |
| Prox | 4.32 | 7.77 | 2.34 | 5.45 | 8.82 | 2.63 | 7.03 | 9.98 | 2.99 | 1.13 | 11% | 21% | 0.29 | 0.65 |
| Mid | 5.37 | 8.53 | 2.61 | 6.22 | 9.48 | 2.81 | 7.57 | 10.11 | 3.11 | 0.85 | 7% | 14% | 0.20 | 0.50 |
| Dis | 4.63 | 7.97 | 2.43 | 5.92 | 9.15 | 2.75 | 7.29 | 9.92 | 3.05 | 1.29 | 12% | 22% | 0.32 | 0.62 |
| Mean | 5.03 | 8.49 | 2.53 | 6.15 | 9.40 | 2.80 | 7.69 | 10.32 | 3.13 | 1.13 | 10% | 18% | 0.27 | 0.60 |
| ±SD | 0.51 | 0.51 | 0.13 | 0.49 | 0.42 | 0.11 | 0.59 | 0.44 | 0.12 | 0.21 | 0.02 | 0.03 | 0.05 | 0.08 |

Tacrolimus Loaded into the Biological Oil

To evaluate this new coating method use was made as endoluminal prosthesis of a commercial available balloon expandable coronary stent (V-Flex Plus, 16 mm/3.0 mm, William Cook Europe). As drug we used Tacrolimus, a calcineurin inhibitor, which blocks IL-2 mediated T-cell proliferation and possesses anti-inflammatory and anti-proliferative activity.

Tacrolimus (1 mg) was dissolved in an emulsion of 50% highly purified eicosapentaenoic (EPA) enriched oil and 50% pure ethanol. After intense stirring during 5 min a homogeneous solution was obtained. Stents were cleaned and degreased and dried. They were dipped in a Sodium bicarbonate solution during 30 seconds, air-dried and than dipped in the Tacrolimus/eicosapentaenoic (EPA) enriched oil/ethanol emulsion.

The stents were air-dried in a warm laminar flow to let evaporate the ethanol and a thin, homogeneous coating layer was obtained. Stents were repeatedly (3×) dipped and dried. Thereafter the stents were immerced in an alfa-tocopherol/ethanol solution and again airdried.

Total Tacrolimus amount obtained on one stent was 800 µg.

In vitro drug release showed a progressive release of the drug over 4 weeks.

In vivo experiments using a porcine coronary model revealed perfect biocompatibility of the coating system. No inflammatory response was seen at 5, 10 days, and 4 and 8 weeks after stent inplantation. Using the coating without the drug an unexpected 20% reduction of in-stent neointimal hyperplasia compared with non-coated bare stents was observed at 4 and 8 weeks. Adding tacrolimus, the neointimal hyperplasia could be further decreased.

The invention claimed is:

1. An intraluminal device, comprising:
   at least one coating containing a therapeutic agent comprised in a therapeutic matrix which covers at least a portion of the device, said therapeutic matrix disposed onto said device to deliver the therapeutic agent to the tissue of a patient upon implantation in said patient, and said therapeutic matrix formed by a bio-compatible oil or fat which has not been subjected to an aggressive polymerization step,
   wherein said bio-compatible oil or fat is fish oil, wherein said fish oil comprises a synthetic fish oil, wherein said therapeutic matrix comprises triglycerides in an amount of more than 70% by weight, and wherein said triglycerides comprise unsaturated omega-3 fatty acids in an amount of more than 15% by weight.

2. The device according to claim 1, wherein said therapeutic agent is dissolved in said fish oil.

3. The device according to claim 1, wherein said therapeutic agent is emulsified or suspended in said fish oil.

4. The device according to claim 1, wherein said therapeutic agent is chemically bonded to said fish oil.

5. The device according to claim 1, wherein said therapeutic agent comprises alpha-tocopherol.

6. The device according to claim 1, wherein said unsaturated omega-3 fatty acids comprise at least one fatty acid selected from a group of fatty acids consisting of eicosapentaenoic and decosahexaenoic acid.

7. The device according to claim 1, wherein said fish oil further comprises alpha-tocopherol acetate.

8. The device according to claim 1, wherein said coating comprises at least 90% by weight of said fish oil.

9. The device according to claim 1, wherein said coating comprises at least 95% by weight of said fish oil and said therapeutic agent.

10. The device according to claim 1, wherein said device is an endovascular prosthesis.

11. The device according to claim 1, wherein said fish oil is liquid at room temperature.

12. The device according to claim 1, wherein said device is provided with a top coat applied on top of said coating.

13. The device according to claim 12, wherein said top coat comprises alpha-tocopherol, in an amount of at least 95% by weight.

14. The device according to claim 1, wherein said therapeutic agent comprises at least one therapeutic agent selected from the group consisting of vinblastine, sirolimus, mitoxantrone, tacrolimus, paclitaxel, cytochalasin, latrunculin, and everolimus.

15. The device according to claim 1, wherein said therapeutic agent comprises at least one therapeutic agent selected from the group consisting of deferoxamine, geldanamycin, nigericin, penitrem, paxilline, verruculogen, KT5720, KT5823, Anisomycin, chelerythrine chloride, genistein, parthenolide, trichostatin A, T2 toxin, Zearalenone, Interferon, epithalon-D, Caionophore, 4 bromo Ca Ionophore, Aflatoxins, aphidicolin, brefeldin A, cerulenin, chromomycin A3, citrinin, cyclopiazonic acid, forsokolin, fumagillin, fumonisins B1, B2, hypericin, K252, mycophenolic acid, ochratoxin A, and oligomycin.

16. The device according to claim 1, wherein said therapeutic agent comprises at least one therapeutic agent selected from the group consisting of immunosuppressants, anti-inflammatories, anti-proliferatives, anti-migratory agents, anti-fibrotic agents, proapoptotics, calcium channel blockers, anti-neoplastics, antibodies, anti-thrombotics, anti-platelet agents, IIb/IIIa blockers, antiviral agents, anti-cancer agents, chemotherapeutics, thrombolytics, vasodilators, antibiotics, growth factor antagonists, free radical scavengers, radiopaque agents, anti-angiogenesis agents, angiogenesis drugs, cyclooxygenase inhibitors, phosphodiesterase inhibitors, cytokine inhibitors, nitrogen oxide donors, cytokine activators, anti-oxidants, radioactive compounds, steroids, and non-steroidal anti-inflammatory drugs.

17. The device according to claim 1, wherein said therapeutic agent comprises at least one therapeutic agent selected from the group consisting of mycophenolic acid, mycophenolate mofetil, mizoribine, methylprednisolone, dexamethasone and other corticosteriods, everolimus, triptolide, methotrexate, benidipine, ascomycin, wortmannin, LY 294002, Camptothecin, Topotecan, hydroxyurea, cyclophosphamide, cyclosporin, daclizumab, azathioprine, and gemcitabine.

18. The device according to claim 1, wherein said device is porous and said at least one coating is applied within pores of the device.

19. The device according to claim 1, wherein said fish oil comprises at least one fatty acid ester selected from a group of fatty acid esters consisting of methyl esters and ethyl esters.

20. The device according to claim 1, wherein said therapeutic agent comprises at least one gene component selected from a group of gene components consisting of a polynucleotide, an oligonucleotide, a recombinant nucleic acid, gene/vector system, and a nucleic acid.

21. The device according to claim 1, wherein said at least one coating comprises a local coating separate from a top coating.

22. The device according to claim 21, wherein said at least one coating comprised of said local coating and said top coating comprises at least one stabilizer selected from a group of stabilizers consisting of a binder, and a thickening agent to stabilize the therapeutic mixture.

23. The device according to claim 1, wherein said matrix provides sufficient lubrication for device deployment without addition of a separate lubricant component.

24. The device according to claim 1, wherein said device comprises at least one device selected from a group consisting of an intraluminal prosthesis, balloon, shunt, catheter and local drug delivery device.

25. A method for providing a device, comprising:
providing said device with at least one coating containing a therapeutic agent comprised in a therapeutic matrix which covers at least a portion of the device, and
applying a bio-compatible oil or fat, which has not been subjected to an aggressive polymerization step, and comprises said therapeutic agent, in a flowable state onto the device to form said therapeutic matrix comprising the therapeutic agent;
wherein said bio-compatible oil or fat comprises a synthetic fish oil and; wherein said therapeutic matrix comprises triglycerides in an amount of more than 70% by weight, and wherein said triglycerides comprise unsaturated omega-3 fatty acids in an amount of more than 15% by weight.

26. The method according to claim 25, wherein said oil or fat is applied in a molten state onto the device.

27. The method according to claim 25, wherein said oil or fat is mixed with a solvent before applying it onto the device and, after having applied the mixture of solvent and oil or fat onto the device, the solvent is allowed to evaporate.

* * * * *

UNITED STATES PATENT AND TRADEMARK OFFICE
CERTIFICATE OF CORRECTION

| | | |
|---|---|---|
| PATENT NO. | : 8,460,693 B2 | Page 1 of 1 |
| APPLICATION NO. | : 10/494892 | |
| DATED | : June 11, 2013 | |
| INVENTOR(S) | : Dhondt et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1512 days.

Signed and Sealed this
Sixth Day of January, 2015

Michelle K. Lee
*Deputy Director of the United States Patent and Trademark Office*